United States Patent [19]

Kaivola

[11] 4,206,750
[45] Jun. 10, 1980

[54] SPECULUM FOR GYNECOLOGICAL ENDOSCOPY EXAMINATION

[76] Inventor: Seppo Kaivola, Linnanherrantie 3 B, 00950 Helsinki 95, Finland

[21] Appl. No.: 943,559

[22] Filed: Sep. 15, 1978

[30] Foreign Application Priority Data

Dec. 15, 1977 [FI] Finland .................................. 773800

[51] Int. Cl.$^2$ ............................................. A61B 1/32
[52] U.S. Cl. ...................................... 128/17; 128/341
[58] Field of Search ......................... 128/3–6, 128/17–19, 242, 244, 303.11, 303.12, 361, 20, 341, 345, 12–14; 81/300, 302, 415, 417

[56] References Cited
U.S. PATENT DOCUMENTS

| 3,731,673 | 5/1973 | Halloran | 128/20 |
| 3,752,149 | 8/1973 | Ungar et al. | 128/20 X |
| 3,769,968 | 11/1973 | Blount et al. | 128/17 |

Primary Examiner—Robert W. Michell
Assistant Examiner—Jeffrey W. Tayon
Attorney, Agent, or Firm—Steinberg & Blake

[57] ABSTRACT

Speculum apparatus for use in connection with gynecological endoscopy examination includes a first substantially L-shaped inner member defined by an elongate first handle portion, a first dilating portion extending angularly with respect to said first handle portion, and a first connecting portion integrally interconnecting the first handle and dilating portions, and a second substantially L-shaped outer member defined by an elongate second handle portion, a second dilating portion extending angularly with respect to said second handle portion, and a second connecting portion integrally interconnecting said second handle and dilating portions. The connecting portion of the outer member is received within the channel shaped interior of the first connecting portion and shoulders defined on the second dilating portion engagingly mate with terminal edges of wall portions provided on the first connecting portion so as to provide a detachable pivotal interconnection between the inner and outer members. An aperture is provided in the outer member connecting portion to provide a direct line of sight between the first and second dilating portions of the apparatus. The inner member preferably comprises a conventional unitary or one-part speculum so that upon detachment of the inner and outer members, the inner member may be used as such.

9 Claims, 5 Drawing Figures

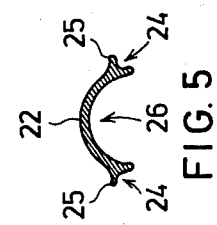
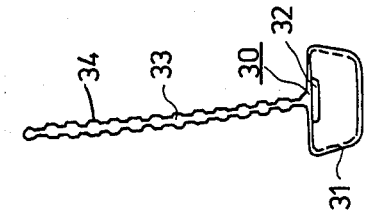
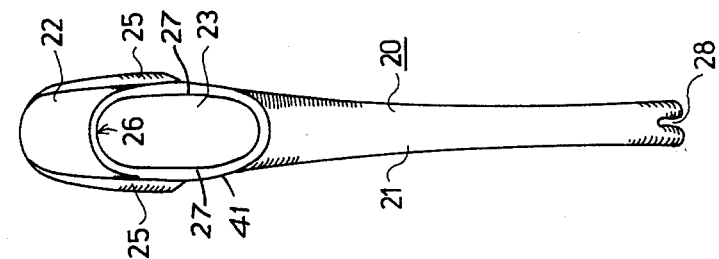
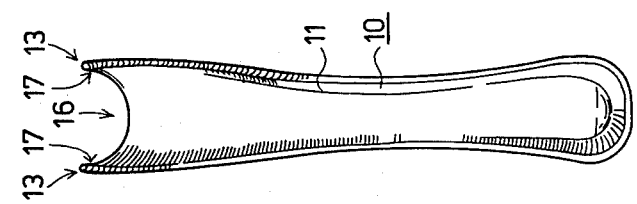
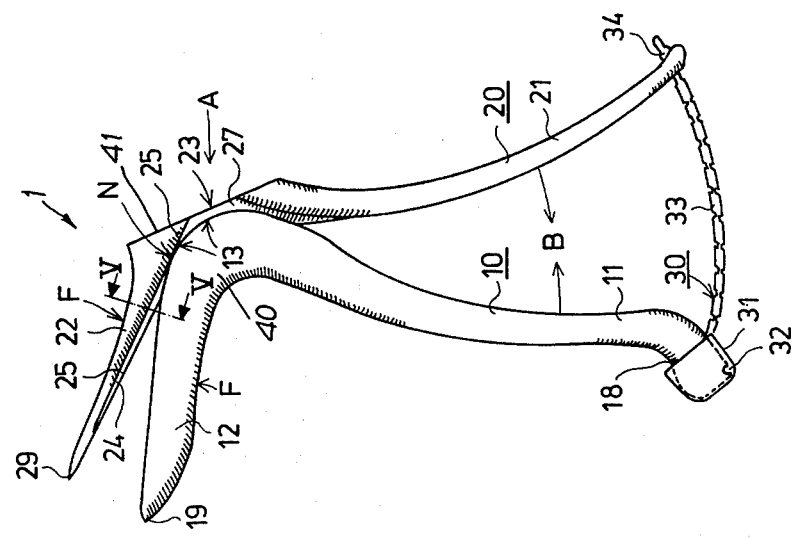

SPECULUM FOR GYNECOLOGICAL ENDOSCOPY EXAMINATION

BACKGROUND OF THE INVENTION

This invention relates generally to medical instruments for gynecological endoscope examinations and, more particularly, to a so-called duck-billed speculum apparatus comprising inner and outer members, each having a substantially L-shaped configuration which are detachably pivotally interconnected to each other, the outer member having a viewing aperture formed therein to provide a direct line of sight between the dilating portions of the speculum.

Specula of the so-called duck-billed type intended for gynecological endoscopy are known. More particularly, specula are known which comprise a pair of members which are pivoted together by a fixed hinge axis. The members define a pair of opposed dilating portions, each having a configuration approximating that of a duck-bill. Thus, when the handle portions of such specula are urged towards each other, the duck-bill dilating portions separate from each other to accomplish the dilation of the particular passage of the body which is being viewed. In some cases, the handle portions of such conventional duck-billed specula are provided with groove and projection structure which facilitates the adjustment of the spacing between the duck-billed dilating portions of the speculum and further for locking the same at the desired portion for the duration of the examination.

Such conventional duck-billed specula have not proven to be entirely satisfactory. Thus, in some instances of endoscopic examination it is desirable to employ a unitary or one-part speculum. Although such unitary specula are conventional, should a physician desire to interchangeably employ a duck-billed speculum as described above and a unitary speculum, it is necessary that both instruments be separately provided. Additionally, conventional duck-billed specula do not always provide an unobstructed view of the particular body passage which is being examined. Further, since conventional specula include a pair of members which are fixedly hinged to each other, it is not always possible to manipulate the same to place the particular portion of the body organ or passage being examined into its most advantageous location for examination. An additional disadvantage in the use of such conventional specula is that the above mentioned groove-projection arrangement for fixing the mutual positions of the dilating portions thereof are relatively complex in manufacture and use.

SUMMARY OF THE INVENTION

Accordingly, one object of the present invention is to provide a new and improved speculum for gynecological endoscope examination.

Another object of the present invention is to provide a new and improved speculum comprising a pair of inner and outer members which are detachably pivotally interconnected so that one of the members may be utilized as a conventional unitary or one-part speculum.

Still another object of the present invention is to provide a new and improved speculum comprising a pair of detachably pivotally interconnected members, one of which may be moved longitudinally with respect to the other in order to bring the body portion being examined into a better position for examination.

Still yet another object of the present invention is to provide a new and improved speculum of the type described above which can be adjusted and locked in a stable position in an easy manner.

A further object of the present invention is to provide a new and improved speculum which is easier to use and less complex in construction than conventional specula.

Briefly, in accordance with the present invention, these and other objects are attained by providing a duck-billed speculum including a first substantially L-shaped inner member and a second substantially L-shaped outer member. Each member is defined by an elongate handle portion, a dilating portion extending angularly with respect to the handle portion and a connecting portion integrally interconnecting the handle and dilating portions. The connecting portion of the inner member has a channel shaped cross section which receives the connecting portion of the outer member. A pair of groove defining shoulders are provided on the dilating portion of the outer member which engagingly mate with a corresponding pair of terminal edges defined on the connecting portion of the inner member to define a pivot point between the inner and outer members such that the inner and outer members are detachably pivotally interconnected. The groove defining shoulders provided on the dilating portion of the outer member are substantially rectilinear so that the members may be moved in a longitudinal direction with respect to each other so that the body portion being examined can be placed in the best possible position for examination.

The inner member is preferably formed in the shape of a conventional unitary or one-part speculum so that should the physician desire to utilize a speculum of this type, it is only necessary for him to disengage the outer member from the inner member.

The connecting portion of the outer member is provided with an aperture therethrough so as to provide a direct line of sight between the respective dilating portion of the speculum.

Further, by virtue of the particular arrangement whereby the inner and outer members are detachably pivotally interconnected as described above, upon the handle portions of the speculum being moved towards each other which, of course, results in the dilating portions opening to a greater extent, the pivot point tends to move rearwardly with respect to the free end portions of the dilating portion thereby providing a stable pivoting action despite the fact that the inner and outer members are not pivotally fixed to each other but are rather pivotally interconnected in a detachable manner.

DESCRIPTION OF THE DRAWINGS

A more complete appreciation of the invention and many of the attendant advantages thereof will be readily appreciated as the same becomes better understood by reference to the following detailed description when considered in connection with the accompany drawings wherein:

FIG. 1 is a side elevation view of the speculum of the present invention;

FIG. 2 is a front view of the inner member of the speculum of the present invention;

FIG. 3 is a front view of the outer member of the speculum of the present invention;

FIG. 4 is a plan view of the locking apparatus of the speculum of the present invention; and FIG. 5 is a section view taken along line V—V of FIG. 1.

DESCRIPTION OF THE PREFERRED EMBODIMENTS

Referring now to the drawings wherein like reference characters designate identical or corresponding parts throughout the several views, the speculum of the present invention, generally denoted as 1, comprises a substantially L-shaped inner member 10 and a substantially L-shaped outer member 20. The inner and outer members 10, 20 are detachably pivotally interconnected in a manner which will be described in detail below.

Referring to FIGS. 1 and 2, the inner member 10 includes a handle portion 11 and a dilating portion 12 having a duck-bill configuration. The handle and dilating portions 11, 12 of inner member 10 are integrally connected by a curved connecting portion 40. As best seen in FIG. 2, the inner member 10 has a channel shaped cross section throughout its length. More particularly, in the preferred embodiment, the handle, dilating and connecting portions of inner member 10 define a continuous channel shaped member.

Outer member 20 of speculum 1 also includes a handle portion 21, a dilating portion 22 formed in the configuration of a duck-bill, and a connecting portion 41 integrally connecting the handle and dilating portions thereof. Connecting portion 41 of outer member 20 has an aperture 23 (FIG. 3) formed therethrough, through which the physician may view the body passage being examined through the space defined between the pair of dilating portions 12, 22 in the direction designated A in FIG. 1.

The inner and outer members 10, 20 defining speculum 1 are preferably formed of plastic material. Further, it is desirable to provide specula 1 in a manner such that it is disposable after use so as to avoid the necessity of resterilization thereof.

Inner and outer members 10, 20 are suitably formed in order to facilitate a detachable pivotal interconnection therebetween. More particularly, connecting portion 40 of inner member 10 has a transverse cross section in the shape of a relatively deep channel 16 (FIG. 2) defined by a pair of substantially parallel opposed side walls 17. Side walls 17 terminate at curved upper edges 13 as seen in FIGS. 1 and 2. Referring to FIGS. 1 and 3, the connecting portion 41 of outer member 20 is provided with a pair of substantially planar parallel walls 27, the distance between the outer surfaces thereof being slightly less than the distance between the inner surfaces of the side walls 17 defined on the connecting portion 40 of the inner member 10. The dilating portion 22 of outer member 20 is provided on its longitudinally extending side edges with shoulders 25 as best seen in FIGS. 1 and 5. Shoulders 25 each define a longitudinally extending, substantially rectilinear groove 24.

In the assembly of speculum 1, the planar walls 27 formed on the connecting portion 41 of outer member 20 are located between the side walls 17 which define the connecting portion 40 of inner member 10 and, further, the grooves 24 defined by the shoulders 25 of the dilating portion 22 of outer member 20 matingly engage the curved upper edges 13 of the connecting portion 40 of inner member 10. In this manner, a pivot point, designated N, is defined at the point at which the grooves 24 engage the upper curved edges 13 of side walls 17 of the inner member 10.

According to one feature of the present invention, it is seen that when handle portions 11, 21, are urged against each other in the direction of arrow B in FIG. 1, the location of pivot N moves rearwardly with respect to the tips 19, 29 of dilating portions 12, 22 of inner and outer members 10, 20. In other words, grooves 24 provided on the dilating portion 22 of outer member 20 engage the edges 13 of side wall 17 of the connecting portion 40 of inner member 10 at points further away from the tip 19 of inner member 10 as handle portions 11, 21 are urged together in a direction of arrow B. The speculum 1 of the present invention is particularly advantageous in use in view of this particular feature whereby pivot point N moves rearwardly upon further opening of dilating portions 12, 22. More particularly, in the use of the speculum according to the present invention during endoscopy, when the physician dilates the particular body passage for viewing by opening dilating portions 12, 22, these dilating portions are subjected to respective forces in the direction of arrows F in FIG. 1. The effect of such resistive forces tends to positively maintain inner and outer members 10, 20 in a pivotally engaged relationship. Further, the inner and outer members 10, 20 are prevented from moving relative to each other during the dilation process by virtue of the fact that the groove defining shoulder 25 formed in the dilating portion 22 of outer member 20 is substantially straight or rectilinear while the upper terminal edges 13 of the connecting portion 40 of inner member 10 are curved. As a consequence, when the handle portions 11 and 21 are urged towards each other in the direction of arrow B, the pivot point N tends to move rearwardly and in this way a stable pivoting of the speculum is achieved despite the fact that inner and outer members 10 and 11 have not been fixedly joined by any permanent hinge, pivot pin or the like.

According to another feature of the present invention, since the inner and outer members 10, 20 are separate from each other and detachably mounted without a fixed pivot axis, the respective dilating portions 12, 22 may be selectively moved longitudinally with respect to each other in order to place the body portion being examined in the best possible position for examination. This feature has proved to be especially useful in the endoscopic examination of the papilla of the uterus.

Referring now to FIGS. 1 and 4, a device 30 for adjusting and locking the inner and outer members 10, 20 in a desired relationship whereby dilating portions 12, 22 can be maintained at the desired degree of separation is illustrated. Locking device 30 comprises a cup-shaped portion 31 and elongate portion 33, one end of which is integrally connected to cup-shaped portion 31. Cup-shaped member 31 is provided with a shoulder 32 while elongate portion 33 has a plurality of locking protuberances 34 formed along its length. A groove is provided at the end of handle portion 11 of inner member 10 (FIG. 1) while the end of handle portion 21 of outer member 20 has a slot 28 formed therein.

The cup-shaped portion 31 is located over the free end of handle portion 11 in a manner such that shoulder 32 is frictionally engaged within the groove formed in the handle portion. In use, when the speculum is opened to the desired extent, the elongate portion 33 is located within slot 28 on handle portion 21 in a manner such that the appropriate locking protuberance 34 is fixedly received therein. The elongate portion 33 of locking device 30 is formed of a suitably semi-rigid material so that upon the appropriate location of the cup-shaped portion and locking protuberance as described above, the handle portions are fixed in position relative to each other thereby maintaining the speculum at the desired extent of opening.

As mentioned above, another feature of the invention is the provision of the inner member 10 in the configuration of a conventional unitary or one-part speculum. Thus, should the physician desire to utilize a unitary speculum, it is only necessary to disengage the outer member 20 from the inner member 10 which, of course, is easily accomplished due to the fact that no permanent connection between the two members is provided.

Obviously, numerous modifications and variations of the present invention are possible in the light of the above teachings. It is therefore to be understood that within the scope of the appended claims the invention may be practiced otherwise than as specifically described herein.

What is claimed is:

1. Speculum apparatus for use in connection with gynecological endoscopy examination comprising:
   a first substantially L-shaped inner member defined by an elongate first handle portion, a first dilating portion extending angularly with respect to said first handle portion, and a first connecting portion integrally interconnecting said first handle and dilating portion, at least said first connecting and dilating portions having transverse channel shaped cross-sections defining on at least said first connecting portion a pair of wall portions having curved terminal edges outwardly extending from said first connecting portion;
   a second substantially L-shaped outer member defined by an elongate second handle portion, a second dilating portion extending angularly with respect to said second handle portion, and a second connecting portion integrally interconnecting said second handle and dilating portions, said second dilating portion having a pair of outwardly extending shoulders; and
   said second connecting portion of said outer member being received within the channel shaped interior of said first connecting portion with each of the pair of terminal edges of said first connecting portion matingly engaging respective ones of the pair of shoulders defined on said second dilating portion, the points of engagement defining a pivot axis between said inner and outer members which is displaceable rearwardly with respect to the free ends of said first and second dilating portions when said first and second handle portions are urged towards each other, whereby said inner and outer members are detachably pivotally interconnected without a separate pivot pin or the like.

2. Speculum apparatus as recited in claim 1 wherein said second connecting portion of said outer member has an aperture formed therethrough such that a direct line of sight is provided through said aperture between said first and second dilating portions.

3. Speculum apparatus as recited in claim 2 wherein each of said pair of outwardly extending shoulders provided on said second dilating portion has a groove defined therein, said groove defining shoulders extending longitudinally along the sides of the second dilating portion in a substantially rectilinear manner, such that portions of said terminal edges of said first connecting portion are received within respective grooves of said second dilating portion 4. Speculum apparatus as recited in claim 2 wherein said second connecting and handle portions are at least partially defined by a pair of substantially parallely extending planar wall portions, said planar wall portions being disposed within the channel shaped interior of said first connecting portion in substantial contiguous relationship with said pair of wall portions defined thereby.

5. Speculum apparatus as recited in claim 2 wherein said first inner member comprises a conventional unitary speculum of one piece construction.

6. Speculum apparatus as recited in claim 1 further including locking means for maintaining said first and second handle portions at fixed positions relative to each other.

7. Speculum apparatus as recited in claim 6 wherein said locking means comprises a cup-shaped portion adapted to be fixed to one of said first and second handle portions and an elongate portion having a plurality of locking protuberances formed along its length, one end of said elongate portion being affixed to said cup-shaped portion, the other of said first and second handle portions including means for securing one of said locking protuberances thereto.

8. Speculum apparatus as recited in claim 7 wherein means are provided on the free end of said one of said first and second handle portions for frictionally engaging and securing said cup-shaped member thereto and said locking protuberance securing means comprises a slot formed in the free end of the other of said first and second handle portions.

9. Speculum apparatus as recited in claim 8 wherein said cup-shaped portion has a shoulder formed in the interior thereof and said free end of said one of said first and second handle portions includes a groove formed therein, said groove adapted to receive said shoulder upon engagement of said cup-shaped portion on said handle portion free ends.

* * * * *